United States Patent [19]

Brantigan

[11] Patent Number: 4,743,256
[45] Date of Patent: May 10, 1988

[54] SURGICAL PROSTHETIC IMPLANT FACILITATING VERTEBRAL INTERBODY FUSION AND METHOD

[76] Inventor: John W. Brantigan, 2108 Bramblewood La., Fremont, Nebr. 68025

[21] Appl. No.: 5,785

[22] Filed: Jan. 22, 1987

Related U.S. Application Data

[63] Continuation of Ser. No. 784,112, Oct. 4, 1985, abandoned.

[51] Int. Cl.$^4$ .............................................. A61F 2/44
[52] U.S. Cl. ........................................ 623/17; 623/16; 623/18
[58] Field of Search ................... 623/17, 18, 66, 16; 128/92 Z, 92 Y, 92 ZW, 92 YM, 92 YJ, 92 YF

[56] References Cited

U.S. PATENT DOCUMENTS

| | | | |
|---|---|---|---|
| 2,677,369 | 5/1954 | Knowles | 128/92 R |
| 3,426,364 | 2/1969 | Lumb | 623/17 |
| 3,855,638 | 12/1974 | Pilliar . | |
| 3,867,728 | 2/1975 | Stubstad et al. | 623/17 |
| 4,206,516 | 6/1980 | Pilliar . | |
| 4,309,777 | 1/1982 | Patil | 623/17 |
| 4,550,448 | 11/1985 | Kenna | 623/16 |
| 4,553,273 | 11/1985 | Wu | 623/17 X |
| 4,599,086 | 7/1986 | Doty | 623/17 |

OTHER PUBLICATIONS

PoroCoat-A Technical Review of Porous-Coated Implants for Biological Fixation-DePuy.
Article "Anterior Discectomy and Interbody Fusion for Lumbar Disc Herniation"-Inoue, M.D. et al Number 183, Mar. 1984.
Article-"Clinical Orthopaedics and Related Research Number 193, Mar. 1985.

Primary Examiner—Richard J. Apley
Assistant Examiner—Alan W. Cannon

[57] ABSTRACT

A surgical prosthetic implant for the vertebral column in the form of a rigid, preferably inert metal, plug having a porous metal surface allowing ingrowth of bone cells for biologic fixation is provided to achieve vertebral interbody fusion for treating or preventing back pain in patients with ruptured or degenerated vertebral discs. The plug forms a strut spanning and maintaining the disc space between adjoining vertebrae and has opposite ends bottomed in channels that are cut into the opposing faces of the vertebrae or opposed faces bottomed on the end faces of adjoining vertebrae. Bone ingrowth into the porous surface of the plug achieves long term biological fixation with living bone. Local bone graft harvested from the channel cuts into the vertebrae to receive the plug supplements the fusion. The implant minimizes or eliminates the need for bone graft material obtained from a second surgical site or from a bone bank and simplifies the method of achieving the interbody fusion.

6 Claims, 2 Drawing Sheets

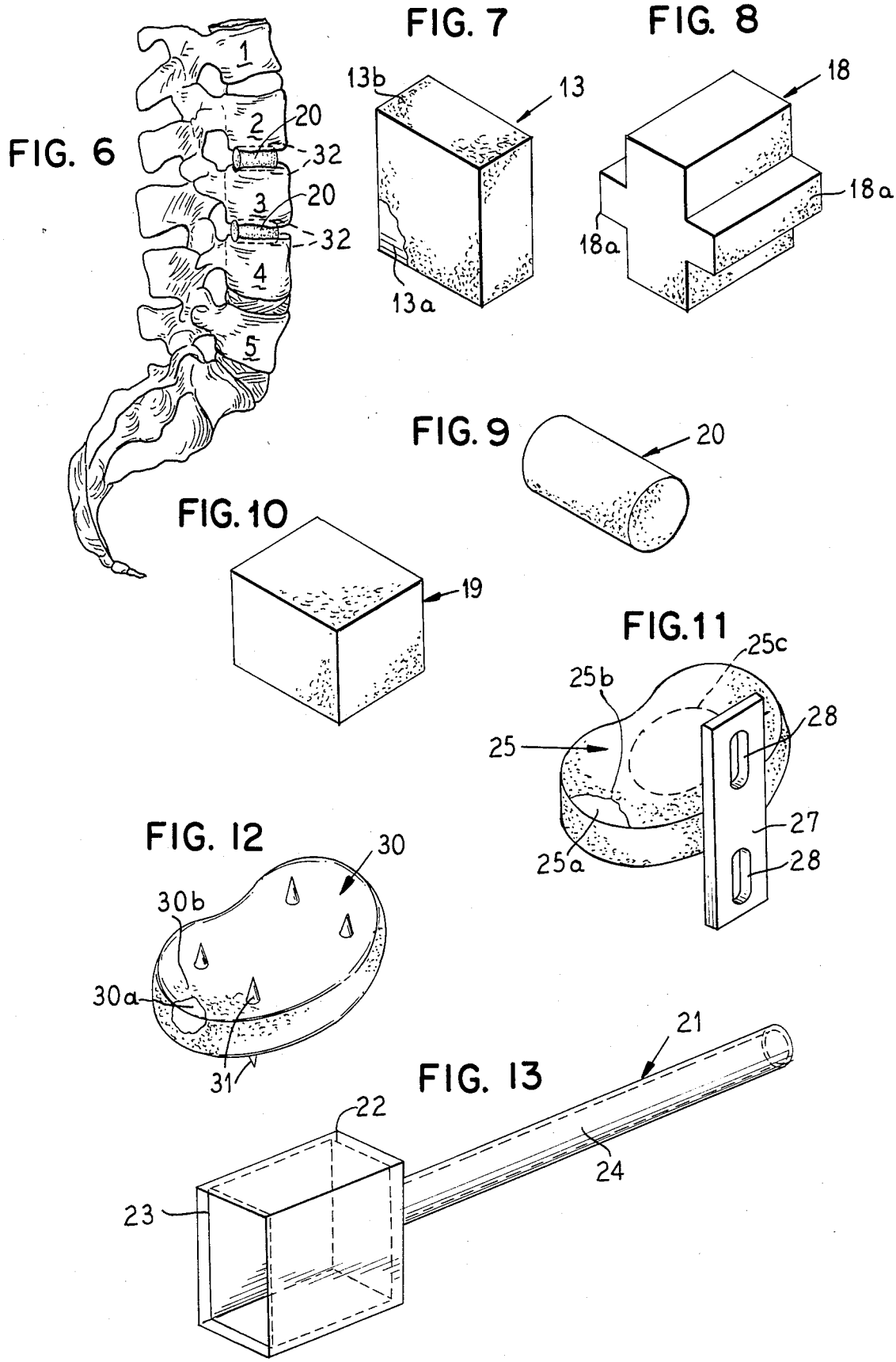

SURGICAL PROSTHETIC IMPLANT FACILITATING VERTEBRAL INTERBODY FUSION AND METHOD

This is a continuation of application Ser. No. 784,112 filed Oct. 4, 1985 abandoned.

BACKGROUND OF THE INVENTION

1. Field of the Invention

This invention relates to the art of prosthetic devices and methods of implanting the same in vertebrae to treat or prevent back pain in patients with ruptured or degenerated intervetebral discs. Specifically, the invention deals with a metal implant plug or block sized and shaped to form a strut between adjoining vertebrae and having a porous surface to promote bone ingrowth, and to methods of implanting the plug.

2. Description of the Prior Art

Low back pain has been a leading cause of industrial disability and a source of enormous economic loss to individuals, corporations and insurance companies. The leading cause of this disability has been from rupture or degeneration of lumbar intervertebral discs. Pain in the lower extremities (sciatica) is caused by compression of spinal nerve roots by damaged discs between the vertebrae and low back pain is caused by collapse of the disc and adverse effects of bearing the majority of the body weight through a damaged unstable vertebral joint. In the past clinical attention has focused on relief of the sciatic pain by removal of pressure from the nerve root. Less success has been achieved with treatment of the low back pain. These surgical treatments have fallen into the following groups:

1. Excision of the Ruptured Soft Disc

This procedure removes the portion of the disc compressing the spinal nerve and is generally successful in relieving the sciatic leg pain but in more than half of the cases, there is a recurrence of back pain. Over a period of time the disc gradually loses height due to the rupture and this loss of height causes the prosterior facet joints of the vertebrae to fit incorrectly resulting in arthritic change in all elements of the spinal segment. Recurrent nerve root compression due to bony encroachment (spinal stenosis) also develops The continuing and recurring back pain from this source has created a leading source of pain and disability.

2. Disc Excision With Posterior Fusion

Traditional posterior fusion, creating bone growth between the bony laminae, or postero-lateral fusion between the transverse processes prevents motion between the adjacent vertebrae but does not alter the fact that approximately 90% of the body weight must be transmitted through degenerated discs causing pain. Further, posterior fusion tends to cause bony overgrowth leading to nerve root compression by spinal stenosis.

3. Disc Excision With Anterior Interbody Fusion

Interbody fusion techniques, in which the soft disc is completely excised and replaced with either the patient's own bone (autologous bone) or with transplant banked bone (homologous bone) are generally successful if solid fusion can be obtained between adjacent vertebrae bodies. Unfortunately, the success rate has only been about 50%.

4. Disc Excision With Posterior Lumbar Intervertebral Fusion (PLIF)

This procedure reconstructs the normal anatomic relationships between the bony and the neural structures and has many advantages. Weight bearing through a solid bony fusion mass between vertebral bodies relieves the mechanical pain of the traditional unstable degenerative disc and generally prevents long term disc collapse or further degenerative changes. The complete disc excision prevents recurrent herniation of the same degenerated disc.

However, this PLIF procedure has several serious disadvantages in that it is technically very difficult, and, therefore, not as successful or widely used as it might be. It entails large amounts of blood loss in a small deep hole causing physiological stress to the patient and psychological distress to the surgeon. Further, the use of autologous bone graft from the patient's own iliac crests extends the operation and creates a second painful operative site. Because it is difficult to obtain a large enough quantity of autogenous bone with sufficient strength, homologous bank bone is generally used.

Interbody bone grafting involves the problems of strength and that of bone incorporation. Strong cortex bone (the outer layer) is required as a strut in the interbody position to prevent collapse of the disc space while healing occurs. The surgeon has the unfortunate requirement of having to fashion the required support struts with handheld tools during the operation and these cortex bone struts are not wide enough for optimum load bearing and they anchor themselves by healing process that occurs very slowly over a matter of years. Further, soft cancellous bone, which heals more reliably over a matter of 12 to 18 months, is also required for a traditional interbody fusion.

It is well understood in orthopaedic surgery, that grafted bone heals by a process called "creeping substitution" in which blood capillaries first grow into the grafted bone, the grafted bone is reabsorbed, and then new bone cells are laid down along the bony matrix of the graft. During the time that the structural bone grafts struts are being reabsorbed, motion must still be prevented in the involved segments and although a brace or cast is often used, the entire process has proven less reliable than desired. Homologous bank bone, being more "foreign", requires a much longer time to grow together and has a higher failure rate estimated at three times the failure as with the patient's own bone. In effect, neither source of bone is optimum for the fusion procedure.

It would be therefore an improvement in this art to provide a surgical procedure for eliminating spinal back pain caused by ruptured or degenerated vertebral discs which overcomes the deficiencies of prior known techniques and, specifically it would be an improvement in this art to span the disc space between adjacent vertebrae with rigid implants having porous surfaces to facilitate bone ingrowth and bottomed in grooves, channels or faces of the adjacent vertebrae so that the implant soon becomes integrated with the vertebrae and provides a permanent weight supporting strut maintaining the disc space.

SUMMARY OF THE INVENTION

According to this invention, rigid plugs of structural material having porous surfaces to facilitate ingrowth of bone tissue are inserted into preformed channels or grooves bridging the cancellous bone of one vertebral body to the cancellous bone of the subjacent vertebual body forming a strut maintaining the disc space between the adjacent vertebral bodies and effective to carry the weight normally supported by the excised or damaged disc. The plugs have opposite ends bottomed in the channels or grooves which are cut into the sides of adjoining vertebrae. The plugs are preferably made of an inert metal substrate such as stainless steel, cobalt-chromium-molybdenum alloys, titanium or the like having a porous coating of metal particles of similar substrate metal, preferably titanium or the like as disclosed, for example, in the Robert M. Pilliar U.S. Pat. Nos. 3,855,683 issued Dec. 24, 1974 and 4,206,516 issued June 10, 1980. These plugs may take the form of flat sided cubical or rectangular slabs, cylindrical rods, cruciform blocks, and the like.

Alternatively, the formation of plug receiving channels in the adjacent vertebrae may be eliminated and the disc space between adjacent vertebrae filled with a plug in the form of a plate bottomed on the cortex bone of the end faces of the adjacent vertebrae and having a thickness spanning the space occupied by the excised disc. These plate-like plugs may be fixedly anchored to the adjacent vertebrae by prongs piercing the adjacent faces of the vertebrae or by providing an upstanding strap on the plate for receiving fasteners such as screws secured in the sides of the adjacent vertebrae.

The insertion of the preformed metal plugs into mortise channel or groove cuts in the vertebral bodies greatly simplifies the technical details of the surgical procedure achieving a much faster fusion with bone ingrowth into the porous surfaces than heretofore achieved with traditional bone grafting techniques. Since the gaps are solidly plugged there is less need to harvest donor bone and the blood loss is much less than with previously known techniques. The plugs can be inserted either posteriorly or anteriorly depending on the surgeon's preference and also on the need for nerve root decompression.

It is then an object of this invention to minimize pain in the lower extremities and low back pain by implanting porous metal plugs in the lower vertebrae which will maintain the space occupied by damaged discs between the vertebrae.

A specific object of the invention is to provide plugs with porous surfaces sized and shaped to be implanted in adjoining vertebrae forming supports maintaining the space normally occupied by the disc between the vertebrae.

A further object of the invention is to provide a surgical technique for inserting support struts between prepared bottoming sites on adjacent lower vertebrae which brings about quick bone growth and fixed fusion of the implant into the vertebral bone structure.

Another object of the invention is to provide a family of prosthetic plugs with porous surfaces sized and shaped to span the space between adjoining vertebrae and having opposed ends fitted in channels formed in the vertebrae.

A further specific object of the invention is to provide a method of fusing together adjacent vertebrae while maintaining the space therebetween normally occupied by the disc wherein channels are cut into the sides of the adjacent vertebrae and rigid plugs are seated and bottomed in these channels.

Other and further objects of this invention will become apparent to those skilled in the art from the following detailed description of the annexed sheets of drawings which show several embodiments of the invention.

FIG. 6 is a side view similar to FIG. 1 but showing the plugs implanted from the posterior side of the vertebral column.

FIG. 7 is a perspective view of one form of implant plug according to this invention.

FIG. 8 is a perspective view of another form of implant plug of this invention.

FIG. 9 is a perspective view of still another form of implant plug according to this invention.

FIG. 10 is a perspective view of still a further form of implant plug of this invention.

FIG. 11 is a perspective view of a plate form of implant plug of this invention.

FIG. 12 is a perspective view of a further plate form of implant plug of this invention.

FIG. 13 is a perspective view of a mortise cutter or chisel to form the channels or grooves for the implant plugs of FIGS. 7–10.

AS SHOWN ON THE DRAWINGS

Figure 1:
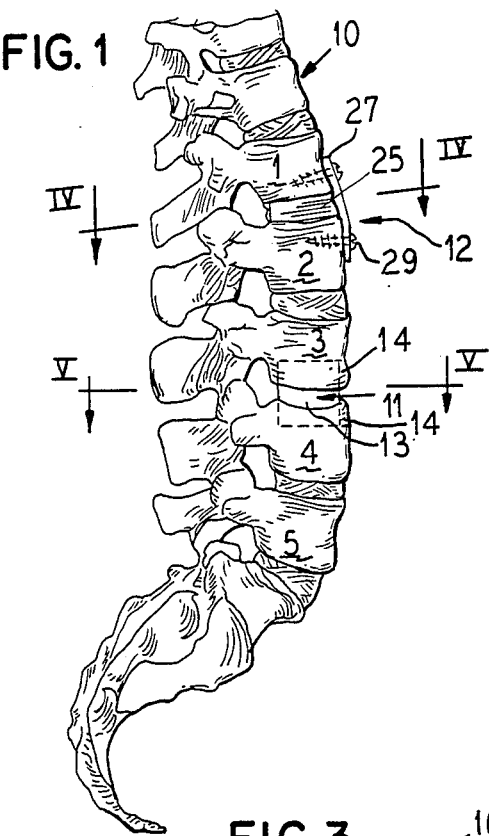
FIG. 1 is a side elevational view of the lower portion of a human vertebral column or back bone including the five lumbar vertebrae and showing two different types of implants between adjoining vertebrae according to this invention.
Figure 2:
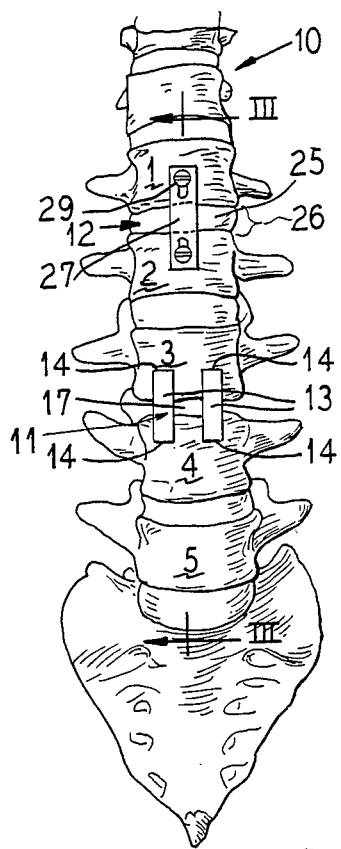
FIG. 2 is an anterior view of the vertebral column with the implants of FIG. 1.
Figure 3:
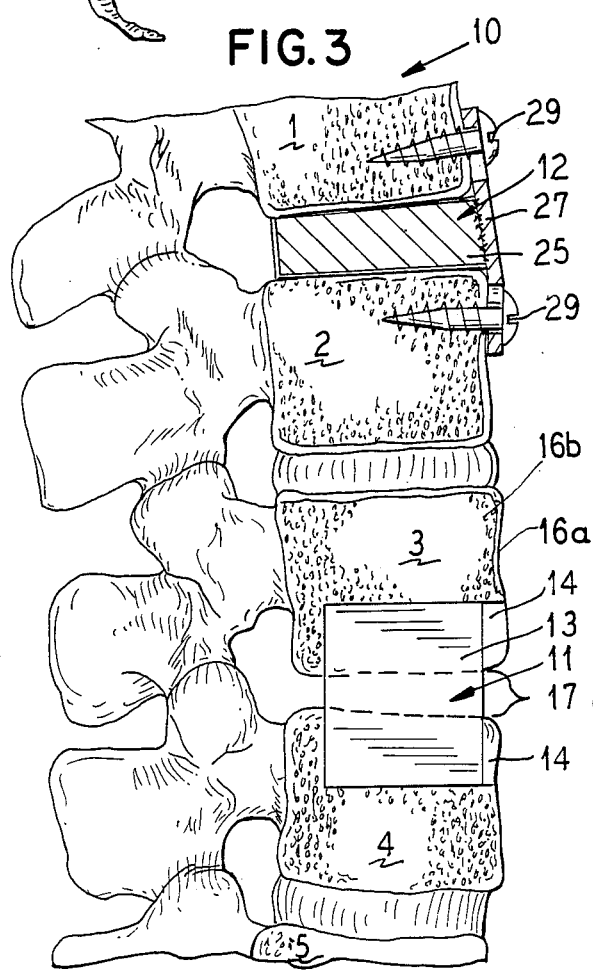
FIG. 3 is an enlarged longitudinal section along the line III of FIG. 2.
Figure 4:
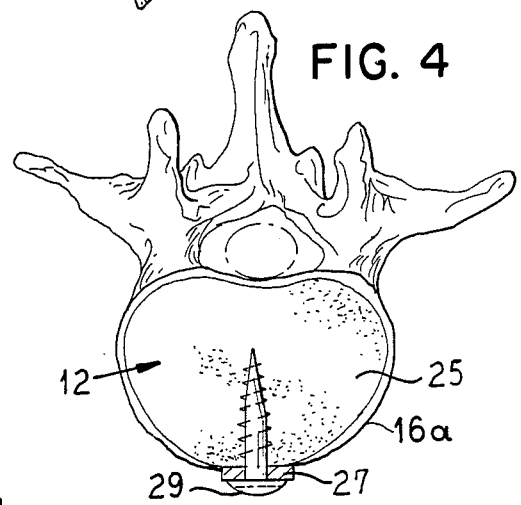
FIG. 4 is a transverse section along the line IV—IV of FIG. 1.
Figure 5:
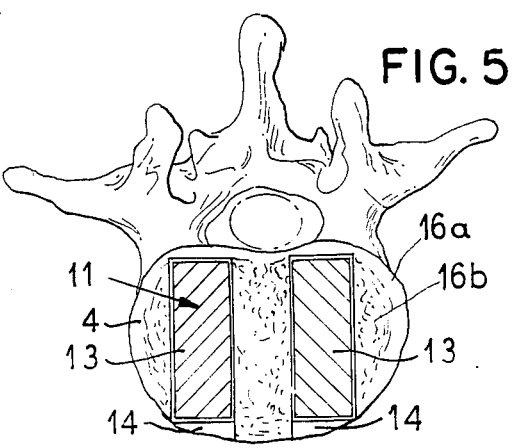
FIG. 5 is a transverse section along the line V—V of FIG. 1.

In FIGS. 1–3 the reference numeral 10 designates generally the lower portion of a human vertebral column including the five lumbar vertebrae numbered 1–5. Vertebrae 3 and 4 are fused together by one form of implant 11 of this invention while vertebrae 1 and 2 are fused together by another form of implant 12 of this invention. These implants 11 and 12 are inserted from the anterior side of the vertebral column 10.

The implant 11 takes the form of two upright side-by-side rectangular plugs of the type shown at 13 in FIG. 7 having a solid inert metal substrate or base 13a and a porous metal coating 13b composed of minute metal balls and beads sintered on the substrate of the type disclosed in the aforesaid Pilliar U.S. Pat. No. 3,855,638 and 4,206,516. This type of plug 13 may have a dimension about 2 cm wide, 2½ cm high, and 1 cm thick. It should be understood, however, that the plug sizes can be varied to suit different conditions.

The sites for bottoming the plugs in adjoining vertebrae are prepared as shown in FIGS. 1–3 and 5 where adjoining ends of the bodies of vertebrae 3 and 4 have a pair of side by side mortise channels 14 cut therein from the anterior faces of the vertebrae bodies to a desired depth for firmly seating the top and bottom ends of two plugs 13. These channels have open anterior ends and closed or blind posterior ends and are preferably long enough to include a portion of the hard cortex of the posterior side of the vertebrae body. The opposite top and bottom ends of the plugs engage the hard cortex bone 16a of the vertebrae body and span the central soft cancellous bone interior 16b. The upstanding heights of the rectangular plugs 13 and the depths of the channels 14 in which they are seated are corrolated to maintain the disc space 17 between vertebrae 3 and 4.

While it is desirable to insert a pair of plugs 12 in spaced upstanding side by side relation as illustrated, some conditions may make it desirable to use a single wider cruciform plug of the type illustrated at 18 in FIG. 8 or a cube shaped plug 19 shown in FIG. 10. These plugs 18 and 19 have top and bottom ends seated in wide single channels cut into the central portions of the adjoining vertebrae. The lateral wings 18a of the plug 18 can radiate into the disc space 17 and bottom on the adjacent faces of the vertebrae.

In other procedures, it may be desirable to provide the plug in the form of a cylindrical rod 20 shown in FIG. 9 with either one or two channels cut into the adjoining vertebral bodies. These channels are arcuately recessed to snugly receive the opposite sides of the rod.

FIG. 13 illustrates generally a chisel tool 21 to form the channels 14. As shown, this tool has a hollow head 22 with a sharp leading cutting edge 23 shaped to cut the flat sided or arcuate channels for receiving the plug implants such as 13, 18, 19, or 20. A shank 24 extends from the head 22 to be imparted by a mallet to drive the cutting edge 23 into the vertebrae bodies.

The surgeon may excise all or only part of a degenerated or herniated disc occupying the space 17 between the adjoining vertebrae and any bone harvested from the cutting of the grooves in the vertebrae may be implanted around the porous plugs to expedite and facilitate bone growth into the pores of the plug.

The implant 12 illustrated between lumbar vertebrae 1 and 2 takes the form of a rigid metal plate 25 shown in FIG. 11 and having a rigid inert metal substrate or base 25a and a porous metal coating 25b of the same type as the plugs 13 and 18-20. The plate is sized and shaped to fit the disc space 26 between vertebrae bodies 1 and 2 and thus, has a thickness sufficient to maintain this space. The anterior side of the plate 25 has an upstanding inert metal strap 27 integrally fixed thereto and provided with a pair of holes 28 receiving screws 29 threaded into the anterior side faces of the adjacent vertebrae 1 and 2. The strap 27 can also have the same substrate and porous coating of the plate 25 or can be uncoated. This plate implant 25 has opposite faces bottomed on the cortex rim bone of adjacent vertebrae and spans the softer interior cancellous bone. If desired, the plate may have a central aperture 25c therethrough illustrated in dotted lines.

The implant 12 does not require a formation of channels in the vertebrae 1 and 2, but the adjacent end faces of the cortex bone of these vertebrae may be cut to better mate with the opposite side faces of the plate 25.

Another type of plate implant plug is illustrated in FIG. 12 where the plate 30, like the plate 25, has an inert metal substrate or body 30a and a porous metal coating 30b and is dimensioned and shaped to fit and maintain the disc space 26 between the adjoining vertebrae 1 and 2. The plug 30 has bone piercing tangs or points 31 projecting from top and bottom faces thereof to penetrate the bodies of the adjoining vertebrae 1 and 2 thereby anchoring the plug in position without requiring the strap and fasteners of the plate 25.

As illustrated by FIG. 6, the channel plugs 13, 18-20 of this invention may also be implanted from the posterior side of the vertebral column with channels 32 being cut diagonally into the sides of the vertebral bodies 2-4. As illustrated these channels are arcuately recessed receiving cylindrical plugs 20 but, of course can be shaped to receive plugs such as 13, 18 and 19. Likewise, the plate type insert 12 may be inserted posteriorly and secured in position from the outer posterior sides of the vertebral bodies. This posterior insertion technique does not give the surgeon the free working space available in anterior insertion techniques.

From the above descriptions, it will be evident to those skilled in this art that the plug implant strut forming technique of this invention greatly increases the success of surgical treatment of the vertebral column in an unobvious manner to stop or relieve back pain.

I claim as my invention:

1. The method of fusing together adjoining vertebrae bodies having spaced opposed faces with a disc space therebetween and peripheral hard cortex bone surrounding soft cancellous bone which comprises cutting transverse opposed channels in said spaced opposed faces open at one end to the sides of the adjoining vertebrae bodies and defined by both hard cortex bone and soft cancellous bone, inserting through said open ends of the transverse channels an inert rigid plug spanning the disc space, bottoming opposite ends of the plug in said channels at least partially on said hard cortex bone to provide a rigid strut spanning and maintaining said disc space, providing irregular non-yielding surfaces on said plug, and facilitating bone ingrowth around said surfaces in bonded relation therewith.

2. The method of fusing together adjacent vertebrae bodies without excising a vertebrae body in a vertebral column and without loss of disc space which comprises preparing opposed transversely extending plug bottoming sites in the opposed faces of the adjacent vertebrae bodies including hard cancellous bone of said bodies, inserting at least one rigid plug with a porous metal coating into the disc space bottomed on the prepared sites including said hard cancellous bone to span the disc space forming a strut between the adjacent vertebrae bodies, and fusing the prepared sites to the coating.

3. The method of claim 1 including the step of cutting each channel from the anterior or posterior sides of the adjacent vertebrae bodies, terminating the cutting in advance of the opposite sides of the adjacent vertebrae to provide a closed end for each channel, inserting the plug through the open end of each channel, and bottoming the plug on said closed end of each channel.

4. The method of claim 1 including the added step of cutting a pair of transverse opposed channels in side-by-side relation in each of said spaced opposed faces, and inserting a separate unitary rigid plug into each pair of opposed channels.

5. The method of claim 1 including the step of cutting fragmental cylindrical opposed channels in said spaced opposed faces and inserting a cylindrical rigid plug endwise into said channels to transversely span the disc space.

6. The method of claim 1 including the step of correlating the depth of the channels and the height of the plug to maintain the disc space.

* * * * *